US010309918B2

(12) United States Patent
Davis et al.

(10) Patent No.: US 10,309,918 B2
(45) Date of Patent: Jun. 4, 2019

(54) QUANTUM CAPACITANCE SENSING

(71) Applicants: OXFORD UNIVERSITY INNOVATION LIMITED, Botley (GB); UNIVERSIDADE ESTADUAL PAULISTA "JÚLIO DE MESQUITA FILHO"-UNESP, Centro, São Paulo (SP) (BR)

(72) Inventors: Jason Davis, Oxford (GB); Paulo Roberto Bueno, São Paulo (BR)

(73) Assignees: Oxford University Innovation Limited, Oxford (GB); Universidade Estadual Paulista "Julio de Mesquita-Filho"—UNESP, Sao Paulo (BR)

( * ) Notice: Subject to any disclaimer, the term of this patent is extended or adjusted under 35 U.S.C. 154(b) by 0 days.

(21) Appl. No.: 15/643,208

(22) Filed: Jul. 6, 2017

(65) Prior Publication Data
US 2017/0370867 A1 Dec. 28, 2017

Related U.S. Application Data

(63) Continuation of application No. PCT/GB2016/050162, filed on Jan. 26, 2016.

(30) Foreign Application Priority Data

Jan. 26, 2015 (GB) .................................. 1501232.1

(51) Int. Cl.
*G01N 27/22* (2006.01)
*G01N 27/02* (2006.01)
(Continued)

(52) U.S. Cl.
CPC ......... *G01N 27/221* (2013.01); *G01N 27/026* (2013.01); *G01N 27/227* (2013.01);
(Continued)

(58) Field of Classification Search
CPC .... G01R 27/2605; G01R 15/16; G01R 27/26; G01D 5/24; G01N 27/22; G01N 27/221
(Continued)

(56) References Cited

U.S. PATENT DOCUMENTS

2003/0211637 A1* 11/2003 Schoeniger ........ G01N 33/5438
436/523
2013/0102031 A1* 4/2013 King ....................... C12P 19/34
435/69.6

(Continued)

FOREIGN PATENT DOCUMENTS

WO  WO 2011/069997  6/2011
WO  WO 2012/009322  1/2012
(Continued)

OTHER PUBLICATIONS

Jia, Yi, and Junbai Li. "Molecular assembly of schiff base interactions: construction and application." Chemical reviews 115.3 (2014): 1597-1621.*

(Continued)

*Primary Examiner* — Christopher P McAndrew
(74) *Attorney, Agent, or Firm* — Klarquist Sparkman, LLP

(57) ABSTRACT

The present application relates to a sensing method that is carried out using an electrode that comprises an electrode substrate functionalized with sensing elements. The method involves conducting electrochemical impedance spectroscopy at a plurality of applied voltages and then integrating measurement data as a function of voltage. Also provided is an apparatus for carrying out the sensing method. The method and apparatus are suitable for a broad range of sensing applications, including the detection of diagnostic biomarkers, drug screening, development of glycoarray sys- (Continued)

tems and the sensing of environmental parameters such as light intensity, temperature and humidity.

17 Claims, 4 Drawing Sheets

(51) Int. Cl.
| | |
|---|---|
| G01N 27/27 | (2006.01) |
| G01N 33/68 | (2006.01) |
| G01R 27/26 | (2006.01) |
| H01L 29/16 | (2006.01) |
| G01N 33/543 | (2006.01) |
| H01L 31/115 | (2006.01) |

(52) U.S. Cl.
CPC ......... *G01N 27/27* (2013.01); *G01N 33/5438* (2013.01); *G01N 33/68* (2013.01); *G01R 27/2605* (2013.01); *H01L 29/1606* (2013.01); *H01L 31/115* (2013.01); *G01N 2333/4737* (2013.01)

(58) Field of Classification Search
USPC ........................................................ 324/686
See application file for complete search history.

(56) References Cited

U.S. PATENT DOCUMENTS

| | | | | |
|---|---|---|---|---|
| 2014/0128285 | A1* | 5/2014 | Rowat | G01N 29/022 506/10 |
| 2014/0145735 | A1 | 5/2014 | Koester | |
| 2014/0342442 | A1* | 11/2014 | Toloue | C12Q 1/6834 435/287.2 |
| 2015/0219579 | A1* | 8/2015 | Davis | G01N 27/3276 205/777.5 |
| 2016/0195520 | A1 | 7/2016 | Davis et al. | |

FOREIGN PATENT DOCUMENTS

| | | |
|---|---|---|
| WO | WO 2014/009747 | 1/2014 |
| WO | WO 2015/022483 | 2/2015 |

OTHER PUBLICATIONS

Slaney, Anne M., et al. "Biocompatible carbohydrate-functionalized stainless steel surfaces: a new method for passivating biomedical implants." ACS applied materials & interfaces 3.5 (2011): 1601-1612.*
Xu, Huilong, et al. "Quantum capacitance limited vertical scaling of graphene field-effect transistor." Acs Nano 5.3 (2011): 2340-2347. APA.*
Dong, Xiao-Chen, et al. "3D graphene-cobalt oxide electrode for high-performance supercapacitor and enzymeless glucose detection." ACS nano 6.4 (2012): 3206-3213.*
Lehr, Joshua, et al. "Label-free capacitive diagnostics: exploiting local redox probe state occupancy." Analytical chemistry 86.5 (2014): 2559-2564.*

Jia, Yi, and Junbai Li. "Molecular assembly of schiff base interactions: construction and application." Chemical reviews 115.3 (2014): 1597-1621. (Year: 2014).*
Slaney, Anne M., et al. "Bioconnpatible carbohydrate-functionalized stainless steel surfaces: a new method for passivating biomedical implants." ACS applied materials & interfaces 3.5 (2011): 1601-1612. (Year: 2011).*
Xu, Huilong, et al. "Quantum capacitance limited vertical scaling of graphene field-effect transistor." Acs Nano 5.3 (2011): 2340-2347. APA (Year: 2011).*
Dong, Xiao-Chen, et al. "3D graphene-cobalt oxide electrode for high-performance supercapacitor and enzymeless glucose detection." ACS nano 6.4 (2012): 3206-3213. (Year: 2012).*
Bueno et al., "Capacitance Spectroscopy: A Versatile to Resolving the Redox Density of States and Kinetics in Redox-Active Self-Assembled Monolayers," *The Journal of Physical Chemistry B* 116(30):8822-8829, Jun. 11, 2012.
Bueno et al., "Supporting Information—Capacitance Spectroscopy: A Versatile to Resolving the Redox Density of States and Kinetics in Redox-Active Self—Assembled Monolayers," *The Journal of Physical Chemistry C* 116(30):8822-8829, 2012.
Bueno et al., "Eluciding Capacitance and Resistance Terms in Confined Electroactive Molecular Layers," *Analytical Chemistry* 85(1):411-417, Nov. 29, 2012.
Bueno et al., "Elucidating Redox-Level Dispersion and Local Dielectric Effects within Electroactive Molecular Films," *Analytical Chemistry* 86(4):1997-2004, Jan. 6, 2014.
Bueno et al., "Measuring Quantum Capacitance in Energetically Addressable Molecular Layers," *Analytical Chemistry* 86(3):1337-1341, Jan. 9, 2014.
Bueno et al., "The Mesoscopic Electrochemistry of Molecular Junctions," *Scientific Reports* 6:18400, DOI: 10.1038/srep18400, Jan. 13, 2016.
Deen et al., "Graphene-Based Quantum Capacitance Wireless Vapor Sensors," *IEEE Sensors Journal* 14(5):1459-1466, Dec. 20, 2013.
Fernandes et al., "Label free redox capacitive biosensing," *Biosensors and Bioelectronics* 50(0):437-440, Jul. 2, 2013.
Lehr et al., "Label-free Capacitive Diagnostics: Exploiting Local Redox Probe State Occupancy," *Analytical Chemistry* 86(5):2559-2564, Feb. 3, 2014.
Olson et al., "Wireless Graphene-Based Quantum Capacitance Sensors for Continuous Glucose Monitoring," *Nanotechnology 2013: Electronics, Devices, Fabrication, MEMS, Fluidics and Computational*, Chapter 3: MEMS & NEMS Devices and Applications, 2:111-114, 2013 (Abstract only).
Patil et al., "Immittance Electroanalysis in Diagnostics," *Analytical Chemistry* 87(2):944-950, Dec. 9, 2014.
Shaw et al., "The Quantum Capacitance Detector: A concept for a pair-breaking radiation detector based on the single Cooper-pair box," *Physical Review B* 79:144511, Apr. 14, 2009.
International Search Report and Written Opinion dated Apr. 29, 2016 for related International Application No. PCT/GB2016/050162.
Search Report dated Jul. 1, 2015 from the United Kingdom Intellectual Property Office for related British Application No. GB1501232. 1.

* cited by examiner

QUANTUM CAPACITANCE SENSING

CROSS REFERENCE TO RELATED APPLICATION

This application is a continuation application of international application No. PCT/GB2016/050162, which is incorporated herein in its entirety.

FIELD

The present invention relates to a method and apparatus for electrochemical sensing by probing the quantum capacitance of a functionalised electrode.

BACKGROUND

Electrochemical techniques have been used in a broad range of sensing applications, for example for the detection and quantification of molecules of diagnostic interest in physiological samples, for sensing toxic gases and for monitoring changes in environmental parameters such as humidity.

Electrochemical impedance spectroscopy (EIS) is a technique that monitors, changes in capacitance or charge-transfer resistance associated with the changes in the local environment of a suitably modified electrode surface. Such changes can include the binding of substances (e.g. of a target species such as a biomarker) to the electrode surface as well as changes in environmental parameters such as temperature. EIS is an attractive technique for sensing applications in view, for example, of its constructional simplicity, sensitivity, selectivity and ready applicability within label-free methodologies.

In recent work it has been shown by the present inventors that electrochemical impedance methods can be applied to resolve a range of charge fluctuations within molecular films confined at electrode surfaces. These comprise changes associated with electronic dipole fluctuation and field induced ionic movement and can be resolved by Electroactive Monolayer Capacitance Spectroscopy according to their specific timescales and surface potential dependence. When these molecular films contain a moiety with orbital states that are energetically accessible (redox active) the electron transfer that results to/from the underlying metallic electrode generates a new, and sensitively potential dependent, charging process at this interface. This faradaic capacitance (known as redox capacitance, $C_r$) is not electrostatic and can be (for high quality molecular films with associated fast rates of heterogeneous election transfer) hundreds of times greater than the Helmholtz contribution. It has been shown that this $C_r$ signature can be integrated into films which are additionally able to recruit specific targets of interest (such as the antigen partners of antibodies). The redox capacitance change can then be used in the establishment of a novel label free biosensing format of high sensitivity, stability and convenience. For more details, reference can be made, for example, to PCT/GB2014/051938 and to Biosensors and Bioelectronics 50 (2013)437-440.

Although these EIS techniques enable a high sensitivity, stable and convenient sensing method, the following can be noted:

(i) Redox capacitance, $C_r$, in effect reports (through capacitance) on the electrochemical activity of the confined redox groups at their optimal electrochemical "half wave potential".

(ii) No information is gathered at any other potentials.

(iii) If the electrochemical activity of the film is perturbed then the measured value of $C_r$ will change. Perturbations due to phenomena other than the specific binding/recognition event (e.g., side reactions/decomposition, changes in solvent or electrolyte penetration) would not necessarily be distinguishable from the binding/recognition event under study.

There is thus a need for alternative, but related, sensing methods, for example based on EIS principles. Particularly attractive would be a sensing method that utilises a simple experimental set-up (e.g. a single working electrode as a probe), that is broadly applicable for the sensing of a range of different parameters, that does not suffer from one or more of the disadvantages with the known methods discussed above, and/or which has high sensitivity and/or selectivity to the chemical substance or other parameter being sensed.

SUMMARY OF THE INVENTION

The present inventors have now identified a new method for sensing changes in the local environment of a suitably functionalised electrode surface. The new method can be carried out using a particularly simple and convenient electrochemical system, which involves just a single working electrode (i.e., a single probe). Furthermore it is not essential that the working electrode is functionalised with redox groups, nor that these redox groups be assumed to be stable.

The new technique developed by the inventors is readily applicable across a wide range of sensing applications, encompassing for example the specific detection of target species in a carrier medium (e.g. detection of diagnostic biomarkers in physiological samples), drug screening procedures, use in glycorray systems and also the sensing of environmental parameters such as ambient humidity, light intensity and temperature in the vicinity of the working electrode.

In more detail, the technique developed by the inventors makes use of a working electrode that is functionalised with sensing elements that are electronically coupled to the underlying electrode. The distribution of electrons between the sensing elements and the electrode has an associated capacitive (and charge dynamic) fingerprint which changes sensitively as the local environment changes.

In the method of the invention, electrochemical impedance measurements are obtained across a range of different applied potentials (rather then the single underlying potential that is applied in a conventional EIS method). From the plurality of measurements obtained at different potentials are obtained measurements of the real and/or imaginary component of the complex capacitance. C' and/or C", as a function of voltage at a fixed frequency (ω). It has been found that integration of the measured C' and C" values over voltage gives an integrated measurement value that intimately reflects, and therefore senses the nature of, the local environment of the working electrode.

Specifically, the present invention provides:

[1] A sensing method comprising:

(A) obtaining, by electrochemical impedance spectroscopy conducted across a range of applied potentials, a plurality of measurements of the complex impedance, Z*, of a system that has a working electrode that comprises an electrode substrate functionalised with sensing elements whose electrochemical response to the applied potentials is sensitive to a change in the local environment of the electrode, the sensing elements having a dimension of from 0.5 to 10 nm;

(B) converting said plurality of measurements of Z* into a plurality of measurements of the real component of the complex capacitance. C' at a selected frequency ω and/or the imaginary component of the complex capacitance, C", at a selected frequency ω;

(C) integrating the measurements of (a) C', (b) C", or (c) any combination of C' and C", at the selected frequency ω as a function of applied voltage to obtain an integrated measurement value; and (D) evaluating the local environment of the electrode from said integrated measurement value.

The sensing method of the invention is suitable for electrochemical sensing by probing the quantum capacitance of a functionalised electrode. It may therefore be referred to as a "quantum capacitance sensing method".

The invention also therefore provides a quantum capacitance sensing method comprising steps (A), (B), (C) and (D) as defined above for the sensing method of the invention.

[2] An apparatus for use in a sensing method, which apparatus comprises:

an electrochemical spectrometer that comprises a working electrode, a counter electrode and a potentiostat, wherein said working electrode comprises an electrode substrate functionalised with sensing elements whose electrochemical response to applied potentials is sensitive to a change in the local environment of the electrode, the sensing elements having a dimension of from 0.5 to 10 nm;

a receiver configured to receive, from said electrochemical spectrometer, input data comprising a plurality of measurements of complex impedance, Z*, across a range of applied potentials; and a processor configured to (i) convert said plurality of measurements of Z* into a plurality of measurements of the real component of the complex capacitance, C', at a selected frequency is and/or the imaginary component of the complex capacitance, C", at a selected frequency ω, and (ii) integrate said measurements of (a) C', (b) C", or (c) any combination of C' and C", at the selected frequency ω as a function of applied voltage to obtain an integrated measurement value. The sensing method may be a quantum capacitance sensing method, i.e. the apparatus may be for use in a quantum capacitance sensing method.

[3] A storage medium storing computer readable code for implementation by a computer or network of computers, the code, when implemented, causing the computer or network of computers to implement the steps of:

obtaining, from an electrochemical spectrometer, input data comprising a plurality of measurements of complex impedance, Z*, across a range of applied potentials;

converting said plurality of measurements of Z* into a plurality of measurements of the real component of the complex capacitance, C', at a selected frequency ω and/or the imaginary component of the complex capacitance, C", at a selected frequency ω; and integrating said measurements of (a) C', (b) C", (c) any combination of C' and C", at the selected frequency ω as a function of applied voltage to obtain an integrated measurement value.

Further preferred features and embodiments are described in the accompanying description and the appended claim.

BRIEF DESCRIPTION OF THE FIGURES

FIG. 1A shows the linear relationship (analytical curve) between the natural logarithm of CRP concentration and the system's electron density.

FIG. 1B shows $C_q e^2$ g(E) variation (obtained from CS measurements) due to the interaction between anti-CRP and CRP in an electroactive molecular layer at varying CRP concentrations (the trend of increasing CRP concentration is indicated). Absolute energies are shown in the top x-axis. The lines are an adjustment of experimental data (represented by dots) to Gaussian expected shape.

FIG. 2A shows measurements of the conductivity due to a variation on electron density at various CRP concentrations (the trend of increasing CRP concentration is indicated).

FIG. 2B shows an analytical curve obtained from the variation on electron conductance on the layer due to the interaction between anti-CRP and CRP.

DETAILED DESCRIPTION

Figure 1A:
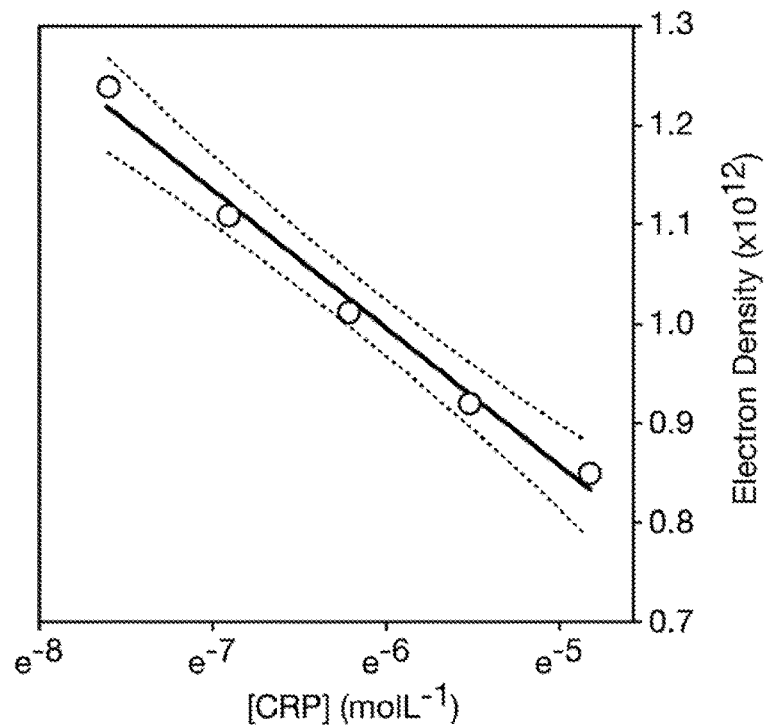
FIGS. 1A and 1B depict analytical curves constructed from the electronic density and its associated DOS variations, obtained as described in the Example.

Optional and preferred features of the present invention are now described. Any of the features described herein may be combined with any of the other features described herein, unless otherwise stated.

The Sensing Method

Electrochemical impedance spectroscopy (EIS) is a technique that is known to the skilled person. Generally, a varying ac potential is applied on a bias (or DC) potential between a working electrode and a counter electrode. Generally, EIS involves scanning across a range of ac frequencies ω. The ratio of the input signal (typically the varying potential) to the output signal (typically the varying current) allows the impedance to be calculated. There is generally a phase difference between the input signal and the output signal, such that the impedance can be considered as a complex function Z*, having a real part (sometimes termed Z') and an imaginary part (sometimes termed Z").

The frequency range of the varying ac potential applied may be from 1 mHz to 10 MHz, The amplitude of the applied ac potential, which is typically in the form of a sine wave, may be from 1 mV to 100 mV, optionally from 5 mV to 50 mV, optionally from 5 mV to 20 mV, optionally from 5 mV to 15 mV, optionally 8 mV to 12 mV, optionally about 10 mV.

When conducting an EIS measurement, the bias potential (or direct current potential) may be set at any desired value. This DC or bias potential is known herein as the applied potential. The method of the present invention involves obtaining a plurality of measurements of the complex impedance across a range of applied potentials (which allows for the subsequent integration over applied voltage), i.e. a number of EIS measurements are obtained each at different selected voltages. Typically the plurality of measurements of the complex impedance obtained by EIS is at least three measurements, preferably at least five measurements, such as at least ten or even at least twenty measurements, i.e. the range of applied potentials typically comprises at least three different applied potentials, preferably at least five different applied potentials, such as at least ten or even at least twenty different applied potentials.

In the step of converting the plurality of measurements of Z* into a plurality of measurements of the real component of the complex capacitance, C', measurements of C' at a (fixed/single) selected frequency $\omega$ are used. As would be well known to a skilled person C' typically varies as $\omega$ changes (i.e. C' is a function of $\omega$). The appropriate selected frequency $\omega$ will of course depend on the construction of a particular electrode and on the nature of the sensing method being undertaken. However, determination of a suitable selected frequency $\omega$ is routine. The skilled person could easily, for example, identify a value of $\omega$ where the obtained values of C' are satisfactorily high (e.g. at or close to the maximum value of C' across the frequency range applied in a routine EIS scan) and/or responsive to the particular characteristic of the electrode's local environment that one is seeking to probe. Analogous principles apply when the plurality of measurements of Z* are converted into a plurality of measurements of the imaginary component of the complex capacitance, C".

Conversion of Z* at the selected frequency $\omega$ into C' and/or C" is routine and well known in the art. In particular, in a standard practical EIS analysis, the complex impedance function Z*($\omega$) at a particular potential can be converted phasorially into complex capacitance C*($\omega$) with its real and imaginary components, using the equation $C^*(\omega)=1/\omega Z^*(\omega)$.

Integration of the measurements of C' and/or C" as a function of applied voltage can also be routinely performed, for example using "area under the graph methods" when C', C" or any combination of C' and C" is plotted against applied voltage and/or by way of well known and routine computerised algorithms for integrating empirically derived data.

It has been found that integration of either C' and C" at the selected frequency $\omega$ as a function of applied voltage provides an "integrated measurement value" that is suitable for sensing, i.e., that can be used to report on the local environment of the electrode when the EIS measurements were conducted. Specifically, an integrated measurement value derived from the integration of C' is related to the density of states (DOS) of the system, i.e. it reflects the quantum capacitance (as exemplified in FIGS. 1A and 1B of the Example). An integrated measurement value derived from the integration of C" is related to the conductance of the system (as exemplified in FIGS. 2A and 2B of the Example).

In practice, it may sometimes be preferable (for pure simplicity of operation) to obtain the integrated measurement value by integration of only one of C' and C" at the selected frequency $\omega$ as a function of applied voltage. In a first preferred embodiment, therefore, the plurality of measurements of Z* is converted into a plurality of measurements of the real component of the complex capacitance, C' at the selected frequency $\omega$ and these measurements are converted as a function of applied voltage to obtain the integrated measurement value. Further, in a second preferred embodiment, the plurality of measurements of Z* is converted into a plurality of measurements of the imaginary component of the complex capacitance, C" at the selected frequency $\omega$ and these measurements are converted as a function of applied voltage to obtain the integrated measurement value.

However, since both C' and C" can be used, it will also be apparent to the skilled person that an integrated measurement value can be obtained by integrating any combination of C' and C", at the selected frequency $\omega$ as a function of applied voltage. For example, any sum of the values of C' and C" (where C' and/or C" are possibly weighted with any negative or positive constants) or any multiple or quotient of the values of C' and C" can be used.

It is therefore to be understood that the term "quantum capacitance sensing method", as used herein, embraces methods in which the integrated measurement value is obtained by integration of only C' at the selected frequency $\omega$ as a function of applied voltage, such that the integrated measurement value reflects the conductance of the system rather than quantum capacitance, as well as methods in which the integrated measurement value is obtained by integration of only C' or by integrating any combination of C' and C", as explained above.

The step of evaluating the local environment of the working electrode is typically performed by comparing the integrated measurement value with one or more reference values. The reference value(s) can be obtained by obtaining one or more corresponding integrated measurement values under conditions where the local environment of the electrode is already known. In other words, the reference value (s) are used to calibrate the integrated measurement value obtained when the method is performed under test conditions with expected values that would be obtained under specific, known conditions. The evaluating of the local environment may be either qualitative or quantitative in nature. Calibration of an apparatus for use in sensing applications is well known and routine in the art, including in methods that are based on EIS.

Working Electrode Construction

The working electrode comprises an electrode substrate functionalised with sensing elements.

The electrode substrate may comprise any electrically conducting material. The substrate may comprise a metal or carbon. The metal may be a metal in elemental form or an alloy of a metal. Optionally, the whole of the substrate comprises a metal or carbon. The substrate may comprise a transition metal. The substrate may comprise a transition metal selected from any of groups 9 to 11 of the Periodic Table. The substrate may comprise a metal selected from, but not limited to, rhenium, iridium, palladium, platinum, copper, indium, rubidium, silver and gold. The substrate may comprise a metal selected from gold, silver and platinum. The substrate may comprise a carbon-containing material, which may be selected from edge plane pyrolytic graphite, basal plane pyrolytic graphite, glassy carbon, boron doped diamond, highly ordered pyrolytic graphite, carbon powder and carbon nanotubes. In a preferred embodiment, the substrate comprises gold, for example the substrate is a gold substrate.

The electrode surface (i.e., the substrate surface) may be planar, which includes a generally flat surface, e.g. without indentations, protrusions and pores. Such substrate surfaces can be readily prepared by techniques such as polishing with fine particles, e.g. spraying with fine particles, optionally in a sequence of steps where the size of the fine particles is decreased in each polishing step. The fine particles may, for example, comprise a carbon-based material, such as diamond, and/or may have particles with diameters of 10 μm or less, optionally 5 μm or less, optionally 3 μm or less, optionally 1 μm or less, optionally 0.5 μm or less, optionally 0.1 μm or less. Following polishing, the substrate surface may be washed, e.g. ultrasonically, optionally in a suitable liquid medium, such as water, e.g. for a period of at least 1 minute, e.g. from about 1 minute to 10 minutes. Optionally, the substrate surface may be washed with an abrasive, e.g. acidic, solution, for example following the polishing and, if used, ultrasonic washing steps. The abrasive solution may comprise an inorganic acid, e.g. $H_2SO_4$, and/or a peroxide, e.g. $H_2O_2$, in a suitable liquid medium, e.g. water. Optionally, the substrates can be electrochemically polished, which may follow any steps involving one or more of polishing with fine particles, washing e.g. ultrasonically and/or using an abrasive solution. The electrochemical polishing may involve cycling between an upper and lower potential until a stable reduction peak is reached, e.g. an upper potential of 0.5 V or more, optionally 1 V or more, optionally 1.25 V or more, and a lower potential of 0.5 V or less, optionally 0.25 V or less, optionally 0.1 V or less.

The electrode substrate is functionalised with sensing elements. The sensing, elements are confined on the electrode surface. In combination with the electrode substrate, the sensing elements are capable of generating an electrochemical response when the EIS is conducted. Furthermore, the electrochemical response to the applied potentials is sensitive to a change in the local environment of the electrode.

These features of the electrode can be achieved by ensuring that the sensing, elements are electronically coupled to the electrode surface. By "electronically coupled" is meant that electrons are capable of redistributing between the electrode surface and the sensing elements. Thus, when the electrode is produced by functionalising the electrode surface with the sensing elements, a redistribution of electrons takes place between the electrode surface and the sensing elements. Similarly, redistribution of elections between the electrode surface and the sensing elements occurs when there is a change in the local environment of the electrode, specifically a change corresponding to the substrate or environmental parameter that is being sensed.

In general the sensing element can be constituted by any chemical compound with a different chemical potential of electrons to that of the electrode. The electrode and the given chemical compound must be separated by very short distance, i.e. within a nanoscale such as lower than 10 nm, e.g. lower then 2 nm. This short distance determines the quantized nature of the transducing signal. Indeed, it connects two energetic states (those of the electrode probe and other from chemical compound itself) by means of a scattering region within nanoscale length.

Consequently, each of the sensing elements typically has a dimension of 10 nm or lower, such as 0.5 to 10 nm, preferably 1 to 5 nm, for example 1 to 3 nm. The said dimension is typically the largest dimension that extends as a straight line from an end of the sensing element that is attached to the electrode surface to an end of the sensing element that is not attached to the electrode surface. Typically all dimensions (i.e., all measurable dimensions) of each of the sensing elements are 10 nm or lower, such as 0.5 to 10 nm, preferably 1 to 5 nm, for example 1 to 3 nm.

A sensing element may consist of a chemical compound with a different chemical potential of electrons to that of the electrode that is coupled to the electrode surface via a short chemical linker, provided that the sensing element (i.e., the said chemical compound and the said linker) has above dimension of 10 nm or lower, such as 0.5 to 10 nm, preferably 1 to 5 nm, for example 1 to 3 nm.

Typically the sensing elements have a finite and confined density of electronic states ("DOS"), in contrast to the underlying electrode substrate which can be regarded to have a substantially infinite DOS. Thus, the sensing elements typically are different from the electrode substrate, i.e. they are not a conductive metal or carbon substrate. Examples of suitable sensing elements include redox active species, a molecular film, nanoparticles, graphene, carbon nanotubes and quantum dots. Functionalisation of electrode substrates with such materials is well known in the art and can be achieved using routine techniques.

Representative examples of suitable redox active species include osmium-based redox systems, ferrocenes, quinones and porphyrins, including derivatives thereof. Derivatives of quinine include p-benzoquinone and hydroquinone. Preferably the redox active species is ferrocene or a derivative thereof, for example an alkyl (e.g., $C_{1-6}$ alkyl) or acyl derivative thereof. Most preferably the redox active species is ferrocene.

Importantly, although the sensing elements may comprise redox active species, it is not essential that the sensing elements are redox active. Thus, in one embodiment of the present invention the working electrode is functionalised with sensing elements, but the working electrode not functionalised with any redox active species. For example, the sensing elements in this embodiment may be selected from a molecular film, nanoparticles, graphene, carbon nanotubes and quantum dots. For example, the sensing elements do not comprise redox active species.

In one preferred embodiment, the sensing elements comprise graphene. Often, for instance, the electrode substrate comprises gold (for example the substrate may be a gold substrate) and the sensing elements comprise graphene. The graphene may be present in oxidised form, i.e. as graphene oxide.

The working electrode may further comprise an intermediate layer disposed between the electrode substrate and the sensing elements. The intermediate layer may be a self-assembled monolayer of a particular compound, e.g. cysteine. The compound in question may be referred to as an insulator.

In one embodiment, the electrode substrate comprises gold, the working electrode further comprises an intermediate layer disposed on the electrode substrate, and the sensing elements, which are disposed on the intermediate layer, comprise graphene. The graphene may be present in oxidised form, i.e. as graphene oxide. The intermediate layer typically comprises cysteine.

The term "sensing elements" can be used interchangeably with the term "nanoscale entities", which also describes the nature of the material functionalised on the electrode surface.

Applications of the Sensing Method

The principles of the present invention can be applied broadly. In particular, it is possible to sense either a physical substance or an environmental parameter other than a physical substance. Substantially any substance or environmental parameter can be sensed provided that a change in the amount of that substance or parameter results in a change in the local environment of the working electrode and thus a change in the distribution of electrons between the sensing elements and the electrode substrate. The working electrode can therefore be designed with regard to the intended sensing method for which it will be used.

Sensing of Physical Substances

In one embodiment, the method is a method for sensing a chemical substance, i.e. a chemical compound or a group of chemical compounds. In this embodiment, in step (A) the working electrode is in contact with a carrier medium that may comprise the substance and the electrochemical response of the sensing elements to the applied potentials is sensitive to the presence of said substance. If the carrier medium does contain the substance then a particular integrated measurement value will be obtained. The integrated measurement value will be different if the carrier medium does not contain the substance. Similarly, changes in the integrated measurement value will occur as the concentration of the substance in the carrier medium changes.

The carrier medium is preferably in liquid form although gaseous media are also be possible. The carrier liquid (or gas) may be any liquid (or gas) in which the substance can be suspended or dissolved (or dispersed). In an embodiment, the carrier liquid comprises water. In an embodiment, the carrier liquid comprises a biological fluid. A biological fluid may be a fluid that has been obtained from a subject, which may be a human or an animal. In an embodiment, the carrier liquid comprises an undiluted biological fluid. An undiluted biological fluid in the present context is a biological fluid obtained from a subject, e.g. a human or animal, that has not been diluted with another liquid. The biological fluid may be selected from blood, urine, tears, saliva, sweat, and cerebrospinal fluid. Optionally, the carrier medium comprises a biological fluid obtained from a subject, e.g. a human or animal, and a diluent. The diluent may be added to the biological fluid after it has been obtained from the subject. The diluent may include a liquid medium, e.g. a liquid medium selected from water and an alcohol, e.g. an alcohol, e.g. ethanol. The carrier medium may further comprise a buffer. The buffer may comprise a phosphate.

In a preferred aspect of this method of the invention, the working electrode comprises receptor moieties that are capable of binding to said substance and the electrochemical response of the sensing elements to the applied potentials is sensitive to the binding of said substance to the receptor moieties. Preferably the receptor moieties are capable of specifically binding to the substance. "Capable of binding specifically to the substance" typically means having a binding constant to the substance at least 50 times greater than the binding constant to any other substance(s) present in the carrier medium, preferably at least 100 times greater and more preferably still at least 200 times greater.

The receptor moieties may be comprised in the sensing elements themselves or alternatively the electrode substrate may be functionalised both with sensing elements and receptor moieties that are different from the sensing elements.

Examples of receptor moieties include antibodies, antibody fragments, nucleic acids, aptamers, oligosaccharides, peptides and proteins. Preferably, the receptor moieties are selected from antibodies, nucleic acids and peptides. Most preferably the receptor moieties are antibodies.

The antibody or the antibody fragment may be selected from one or more of the classes IgA, IgD, IgE, IgG and IgM. In a preferred embodiment, the antibody or antibody fragment is of the IgG type. The antibody binds selectively to the substance of interest. The antibody or antibody fragment may be derived from a mammal, including, but not limited to, a mammal selected from a human, a mouse, a rat, a rabbit, a goat, a sheep, and a horse. The aptamer, may be selected from a peptide aptamer, a DNA aptamer and a RNA aptamer.

The antibody may for instance be anti-alpha synuclein antibody (anti $\alpha$-sync).

Clearly, the choice of receptor moieties for a given electrode is determined by the identity of the substance of interest, i.e. the "target" of interest.

For instance, the target may be alpha synuclein ($\alpha$-sync), in which case the receptor moieties typically comprise, or consist of anti-$\alpha$-sync.

In one embodiment the working electrode comprises receptor moieties; the sensing elements comprise graphene; and the electrode substrate comprises gold. The receptor moieties may be as further defined above, for instance they may comprise or consist of anti-$\alpha$-sync. The graphene may be present in oxidised form, i.e. as graphene oxide, as this may facilitate attachment of the receptor moieties.

The working electrode may further comprise an intermediate layer disposed on the electrode substrate, between the electrode substrate and the sensing elements. The intermediate layer typically comprises cysteine.

Detection of a Target Species, e.g. for Diagnostic Applications

The substance may be a target species, i.e. a species that may or may not be present in the carrier medium, optionally together with one or more other non-target species, and which the users wishes to detect/sense. Most typically the method is one for determining the concentration of said target species in said carrier medium.

Although this method can be used to detect a range of target species, one particularly useful aspect is the detection of a species of diagnostic interest. The sensitive detection of biomarkers in physiological samples is of ever growing interest in diagnosis. The methods of the present invention can be used in order sensitively and selectively to sense (and determine the concentration) of specific biomarkers, specifically by providing an electrode substrate that is functionalised with receptor moieties that are capable of specifically binding to the biomarker of interest.

Examples of target species include those selected from the group consisting of CRP protein, insulin and a marker of one or more of neurodegeneration, cancer, myocardial infarction, diabetes and general trauma.

More generally, suitable target species for detection in accordance with the methods of the invention include proteins, polypeptides, antibodies, nanoparticles, drugs, toxins, harmful gases, hazardous chemicals, explosives, viral particles, cells, multi-cellular organisms, cytokines and chemokines, ganietocyte, organelles, lipids, nucleic acid sequences, oligosaccharides, chemical intermediates of metabolic pathways and macromolecules. In preferred embodiments, the target species comprises, consists essentially of, or consists of, a biological molecule, more suitably a biological macromolecule, most suitably a polypeptide. A biomarker is one example of a biological molecule of particular interest.

If the target species is or comprises a protein, the protein may be selected from, but is not limited to, native proteins, denatured proteins, protein fragments, and prokaryotically or eukaryotically expressed proteins. Protein may have its normal meaning in the art, and most preferably 'protein' refers to a polypeptide molecule. Such polypeptide may comprise modifications such as glycosylation; phosphorylation or other such modifications.

If the target species is an antibody, the antibody may be selected from one or more of the classes IgA, IgD, IgE, IgG and IgM.

If the target species is a nanoparticle, the nanoparticle can be selected from, but is not limited to, one or more of insulating, metallic or semiconducting nanoparticles.

If the target species is a drug, the drug may be selected from, but is not limited to, alcohol (e.g. ethanol), amphetamines, amyl nitrate, heroin, ketamine, anabolic steroids, LSD, solvents, cannabis, cocaine (such as cocaine hydrochloride or 'coke'), tobacco, tranquilisers, crack (i.e. cocaine free base), ecstasy and/or gammhydroxybutyrate (GHB). Alternatively, in some embodiments, the drug may be a medicinal substance.

The target species may be a candidate drug, e.g. at chemical or biological entity that may be tested or screened for a particular activity or property using the present invention.

If the target species is a toxin, the toxin may be selected from, but is not limited to, one or more toxins originating from animals, plants, or bacteria.

If the target species is a viral particle, the viral particle may be selected from, but is not limited to, one or more viral particles with and without a genome.

If the target species is a cell, the cell may be selected from, but is not limited to, one or more of pluripotent progenitor cells, human cells (e.g. B-cells, T-cells, mast cells, phagocytes, neutrophils, eosinophils, macrophages, endothelial cells), cancerous cells (e.g. those originating from liver, cervical bone, pancreatic, colorectal, prostate, epidermal, brain, breast, lung, testicular, renal, bladder cancers), unicellular organisms of non-human origin, algae, fungi, bacteria, plant cells, parasite eggs, plasmodia and mycoplasma.

If the target species is an organelle, the organelle may be selected from, but is not limited to, one or more of nucleus, mitochondria, Golgi apparatus, endoplasmic reticulum, lysosome, phagosome, intracellular membranes, extracellular membranes, cytoskeleton, nuclear membrane, chromatin, nuclear matrix and chloroplasts.

If the target species is a lipid, the lipid may be selected from, but is not limited to, one or more of signalling lipids, structural lipids, phospholipids, glycolipids and fatty acids.

If the target species is nucleic acid sequence, the nucleic acid sequence may be selected from, but is not limited to, one or more of DNA, cDNA, RNA, rRNA, mRNA, miRNA and tRNA.

If the target species is an oligosaccharide, the oligosaccharide may be selected from, but is not limited to, one or more of oligosaccharides of human, animal, plant, fungal or bacterial origin.

The target species may be any antigen or analyte that is indicative of a particular disease. The target may be selected from, for example, C-reactive protein (CRP protein), angiotensin I converting enzyme (peptidyl-dipeptidase A) 1; adiponectin; advanced glycosylation end product-specific receptor; alpha-2-HS-glycoprotein; angiogenin, ribonuclease, RNase A family, 5; apolipoprotein A-1; apolipoprotein B (including Ag(x) antigen); apolipoprotein E; BCL2-associated X protein; B-cell CLL/lymphoma 2; complement C3; chemokine (C—C motif) ligand 2; CD 14, soluble; CD 40, soluble; cdk5; pentraxin-related; cathepsin B; dipeptidyl peptidase IV; Epidermal growth factor; endoglin; Fas; fibrinogen; ferritin; growth hormone 1; alanine aminotransferase; hepatocyte growth factor; haptoglobin; heat shock 70 kDa protein 1 B; intercellular adhesion molecule 1; insulin-like growth factor 1 (somatomedin C); insulin-like growth factor 1 receptor; insulin-like growth factor binding protein 1; insulin-like growth factor binding protein 2; insulin-like growth factor-binding protein 3; interleukin 18; interleukin 2 receptor, alpha; interleukin 2 receptor, beta; interleukin 6 (interferon, beta 2); interleukin 6 receptor; interleukin 6 signal transducer (gp130, oncostatin M receptor); interleukin 8; activin A; leptin (obesity homolog, mouse); plasminogen activator, tissue; proopiomelanocortin (adrenocorticotropin/beta-lipotropin/alpha-melanocyte stimulating, hormone/beta-melanocyte stimulating hormone/beta-endorphin); proinsulin; resistin; selectin e (endothelial adhesion molecule 1); selectin P (granule membrane protein 140 kDa, antigen CD62); serpin peptidase inhibitor, clade E (nexin, plasminogen activator inhibitor type 1), member 1; serum/glucocorticoid regulated kinase; sex hormone-binding globulin; transforming growth factor, beta 1 (Camurati-Engelmann disease); TIMP metallopeptidase inhibitor 2; tumor necrosis factor receptor superfamily, member 1 B; vascular cell adhesion molecule 1 (VCAM-1); vascular endothelial growth factor; Factor II, Factor V, Factor VIII, Factor IX, Factor XI, Factor XII, F/fibrin degradation products, thrombin-antithrombin III complex, fibrinogen, plasminogen, prothrombin, and von Willebrand factor and the like. Markers useful for diabetes include for example C-reactive protein, glucose; insulin; TRIG; GPT; HSPA1 B; IGFBP2; LEP; ADIPOQ; CCL2; ENG; HP; Il2RA; SCp; SHBG; and TEMP2. Currently preferred target species include a target species selected from the group consisting of CRP protein, insulin and a marker of one or more of neurodegeneration, cancer, myocardial infarction, diabetes and general trauma.

The target species may, for instance, comprise or consist of alpha-synuclein (α-sync). If the target species is or comprises α-sync, the receptor moieties may comprise or consist of an α-sync antibody.

The target species may be a target associated with monitoring diabetes. In an embodiment, the target may be selected from glucose, insulin, Interleukin 2 receptor alpha (IL2-RA), C-reactive protein (CRP) and glycated hemoglobin (HbA1c). If the target species is glucose, the receptor moieties may be selected from, for example, the molecular recognition element of GDH-FAD assay, or a glucose/galactose binding protein ("GGBP") (Scholle, et al., Mol. Gen. Genet 208; 247-253 (1987)). If the target is IL-2RA, the receptor moieties may comprise or consist of a monoclonal antibody specific for IL-2RA. If the target species is or comprises C-reactive protein, preferably this is human C-reactive protein. If the target species is or comprises C-reactive protein, the receptor moieties may comprise or consist of anti-CRP. If the target species is or comprises insulin, the receptor moieties may comprise of consist of an insulin antibody.

Glycoarray-Based Methods

The methods of the invention can also be used in applications that involve glycoarrays. A glycoarray is an array in which each array unit comprises specific carbohydrate moieties (that differ from the carbohydrate moieties in the other array units). In the context of the present invention, the array comprises a plurality of separately addressable electrochemical systems, the working electrode of each of which is functionalised with receptor moieties that are carbohydrate moieties. For example, the array of carbohydrate moieties may constitute the glycome or a portion of the glycome of an organism, such as a human.

Thus, in an embodiment of the method of the invention the substance (that is being sensed) is selected from a lectin protein, a glycoenzyme and a carbohydrate-binding antibody, while the receptor moieties are carbohydrate moieties. Furthermore, in this sensing method the working electrode may form part of a glycoarray comprising a plurality of working electrodes each functionalised with different carbohydrate moieties. The method may thus comprise performing the method steps (A)-(D) an each of the working electrodes comprised in the glycoarray.

Drug Screening/Discovery

Another application for the methods of the invention is in the field of drug screening and discovery. In known array-based systems for drug screening, each array unit comprises accessible receptor moieties to which binding by a drug candidate would prima facie indicate that the drug candidate may be of therapeutic interest. For example, there are known screening methods that are based on the taxol-tubulin model. In this model, the interaction activity of the known anti-cancer drug taxol with tubulin protein is used as a reference against Which new drug candidates are compared.

In particular, in the method of the invention the substance (being sensed) may be a drug candidate and the receptor moieties may be moieties that are capable of binding to a known reference drug. Thus, sensing of binding of the drug candidate to the receptor moieties would be correlated with the drug candidate behaving in an analogous manner to the known reference drug (and therefore being worthy of further study). By contrast, failure to bind may lead to rejection of the drug candidate.

It will appreciated that in this sensing method the working electrode may form part of an array comprising a plurality of working electrode each functionalised with said receptor moieties, said array thereby being suitable for use the simultaneous screening of a plurality of drug candidates. This array set-up enables high throughput screening of many drug candidates at a time.

Sensing of Environmental Parameters

In a still further embodiment, the method is a method for sensing a change in an environmental parameter in the local environment of the electrode. Examples of such environmental parameters include the temperature of the local environment, the light intensity in the local environment (e.g., intensity of visible light, or alternatively of additionally the intensity of UV light) and the humidity in the local environment.

In such methods, the interaction of the light, temperature or ambient/surface water affects the measured DOS or electron density (obtained from the integrated DOS) at the sensing elements. The associated change in electrochemical response is measurable and can be readily calibrated for subsequent application.

Apparatus

The present invention also provides an apparatus for use in a sensing method, typically a sensing method, of the present invention. This apparatus comprises an electrochemical spectrometer whose working electrode is functionalised with sensing elements, i.e. an electrochemical spectrometer that is specially adapted for performing the method of the present invention. The working electrode is as described herein.

The apparatus further comprises (a) a receiver configured to receive, from said electrochemical spectrometer, input data comprising a plurality of measurements of complex impedance, $Z^*$, across a range of applied potentials; and (b) a processor configured to (i) convert said plurality of measurements of $Z^*$ into a plurality of measurements of the real and/or imaginary component of the complex capacitance, $C'$ and/or $C''$, at a selected frequency $\omega$, and (ii) integrate said measurements of $C'$, $C''$ or combination of $C'$ and $C''$, at the selected frequency $\omega$ as a function of applied voltage to obtain an integrated measurement value. The receiver and processor can be part of a computer. The functionality of the receiver and processor can be achieved by programming the computer to receive input data from the method of the invention and to process these data into an integrated measurement value as described herein.

The receiver can receive the input data either directly from the spectrometer, or indirectly, for example by reading the data from a data file created by the spectrometer.

By "programming" it is meant that the computer is provided with computer-readable code providing instructions for carrying out the steps of receiving the input data, converting into real and/or imaginary parts of complex capacitance, $C'$ and/or $C''$, and integrating to obtain an integrated measurement value in an automatic fashion, e.g. without intervention from a user. The computer may for example comprise a physical computer that is programmed with a suitable computer program. That program could, for example, be provided on a storage medium for implementation by the computer, or a network of computers. The storage medium could be an integral part of, the computer itself, such as a hard disc, or a removable storage medium such as an optical disc or portable storage device such as a USB flash memory device.

The apparatus can thus be used to carry out a method of the present invention, whereby an operator conducts the necessary EIS measurements of step (A) of the method of the invention using the electrochemical spectrometer and wherein the subsequent steps are then automatically performed to complete the sensing method.

The computer may be further programmed to output data generated from said integrated measurement value. That output may be to a display and/or to a computer file and/or as a data stream to another device. Such data may comprise simple numerical data corresponding to the integrated measurement value itself. Alternatively, the data may comprise an indication of the presence, absence or concentration of a substance being sensed or a qualitative or quantitative indication of a sensed environmental parameter in the system under study. As will be evident to the skilled person, the computer can routinely be programmed to provide such data by additionally programming it with calibration (reference) values relating to the integrated measurement value.

Still further, the invention provides a storage medium storing computer readable code. When implemented, this code is capable of causing a receiver and processor as defined herein (i.e., as a computer as explained above) to perform the steps associated with the receiver and processor in the apparatus of the present invention.

Example 1

A working electrode was prepared as follows, Mixed Self-Assembled Monolayers (SAM) were generated on a gold electrode substrate by incubation in a solution of pentadecanethiol and 11-Ferrocenyl-Undecanethiol. Receptive surfaces were prepared by immersion of these in Anti-CRP.

C-Reactive Protein (CRP) aliquots were added to the interface with concentrations ranging from 0 nmol/L to 8.0 nmol/L in PBS (specifically, measurements were taken at concentrations of 0, 0.5, 1.0, 2.0, 4.0 and 8.0 nmol/L). Electrochemical measurements were performed with a potentiostat using a three-electrode configuration with Ag/AgCl as a reference, platinum as a counter, and the above working electrode. All experiments were carried out in triplicate and measurement values presented in FIGS. 1A, 1B, 2A and 2B are mean values averaged accordingly.

Electrochemical impedance spectroscopy measurements were undertaken across a range of potentials between +0.2V and +0.8V versus Ag/AgCl with a potential step of 15 mV and a steady frequency of 20 mHz.

Figure 1B:
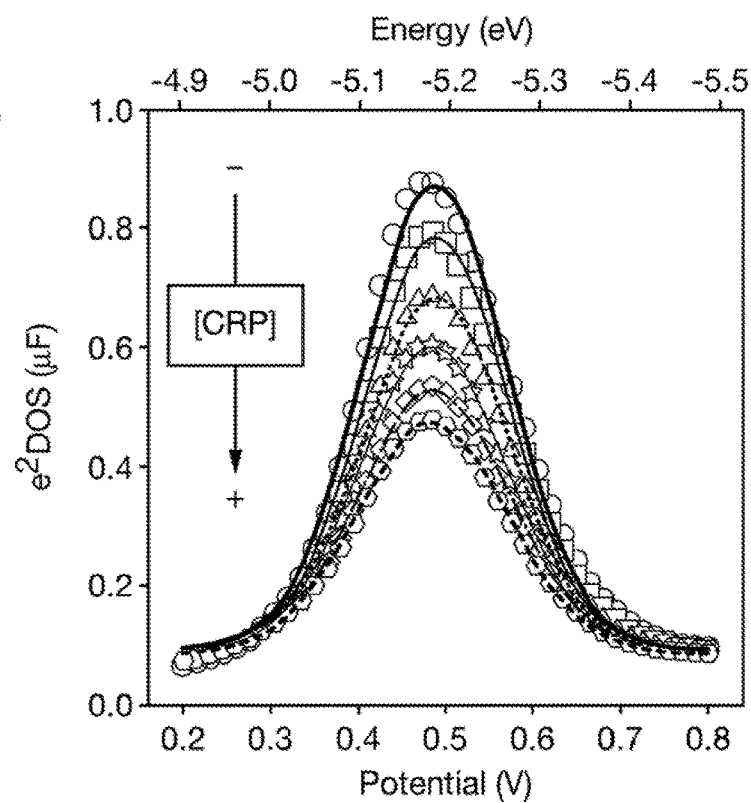
Figure 2A:
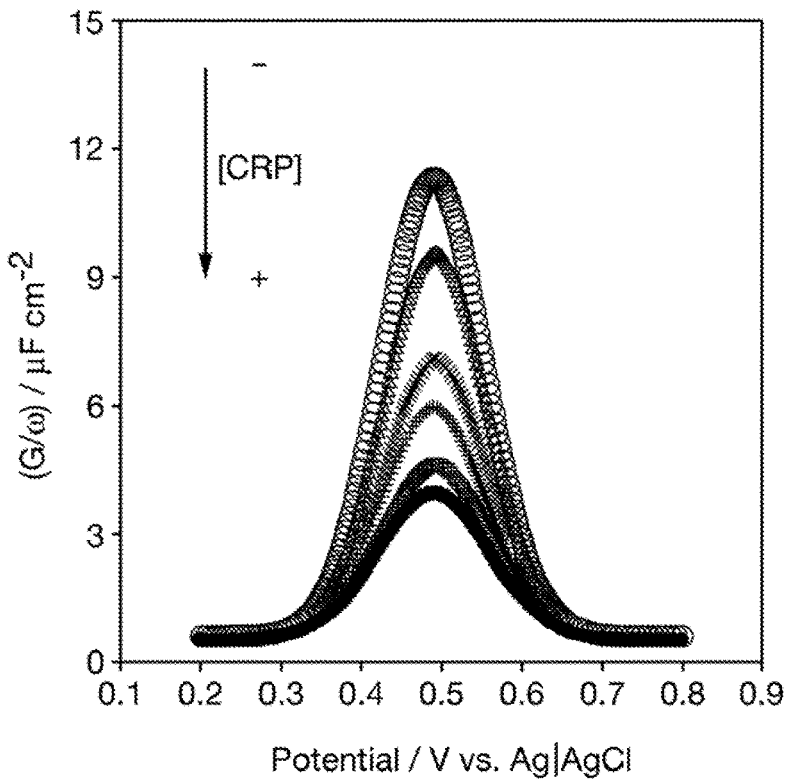
FIGS. 2A and 2B depict conductance changes and an associated analytical curve, obtained as described in the Example.
Figure 2B:
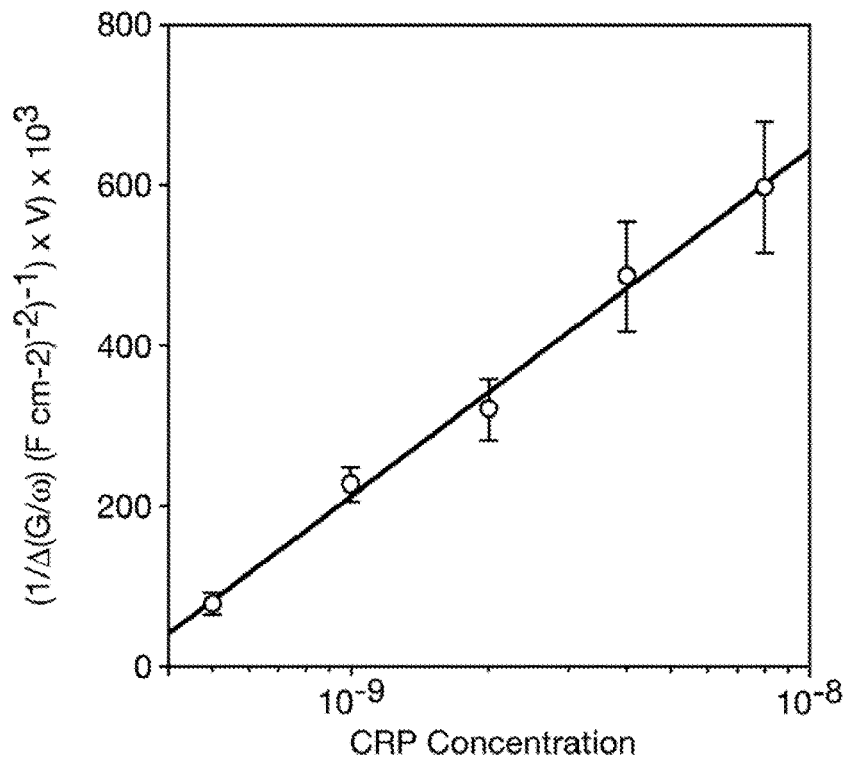

The DOS of FIGS. 1B and 2B were thus obtained. The FIG. 1B shapes were constructed directly from the real part of the complex capacitance at 20 MHz. Specifically the DOS shape reflects quantum capacitance shape, i.e. $e^2$DOS. The lines are a fitting of experimental data (represented by the dots here) to a Gaussian that incorporates the effects of thermal broadening. Thus, the electron density, N, (with thermal broadening) is given by the integral of this Gaussian as $$N = \int_{-\infty}^{\infty} \frac{g_r(\mu_e)}{1 + \exp\left[\frac{E_r - \mu_e}{k_B T}\right]} d\mu_e$$

where: $g_r(\mu_e)$ is the DOS function (Gaussian as a function of potential as shown in FIG. 1B), $E_r$ is the redox potential of the redox species associated with the electrode, $k_B$ is the Boltzmann constant, T is the absolute temperature and $\mu_e$ is the chemical potential of the electrons in the electrode, related to the potential as $\mu_e = -cV$.

N was then accounted as a function of CRP concentration, as shown in FIG. 1A. Specifically, the electron density was calculated by integration of the curves in FIG. 1B normalized by the molecular layer volume (a 3.5 nm length was used for the 11-ferrocenyl-undecanethiol molecular layer).

FIGS. 2A and 2B were constructed from the imaginary capacitance term of the complex capacitance at 20 mHz; it accounts for the conductance of the redox film (see FIG. 2A). The integral of the conductance also provides an electron density. This electron density also provides a means of sensing binding events at the molecular film (see analytical curve shown in FIG. 2B).

Example 2

Figure 3:
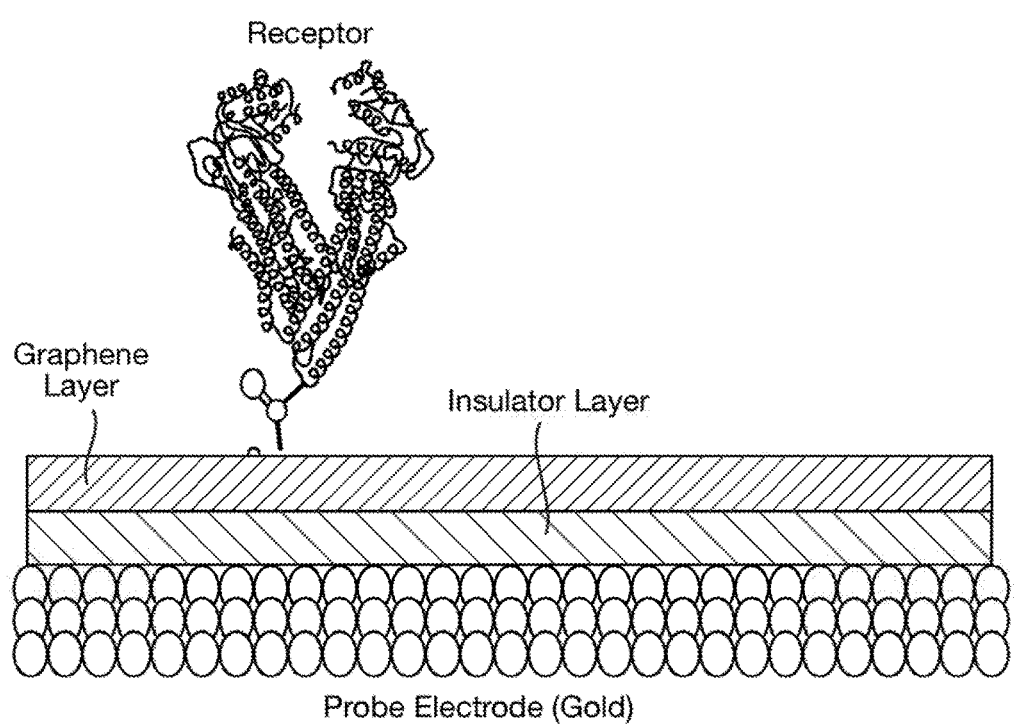
FIG. 3 is a schematic representation of a working electrode (gold) functionalised with sensing elements that are electronically coupled to the underlying electrode. In this example, a sheet of graphene is mounted on the electrode and a protein serving as a receptor to a target analyte is bound to the graphene. The density of states (quantic states), measured experimentally by capacitance spectroscopy, was used as transducer signal.
Figure 4:
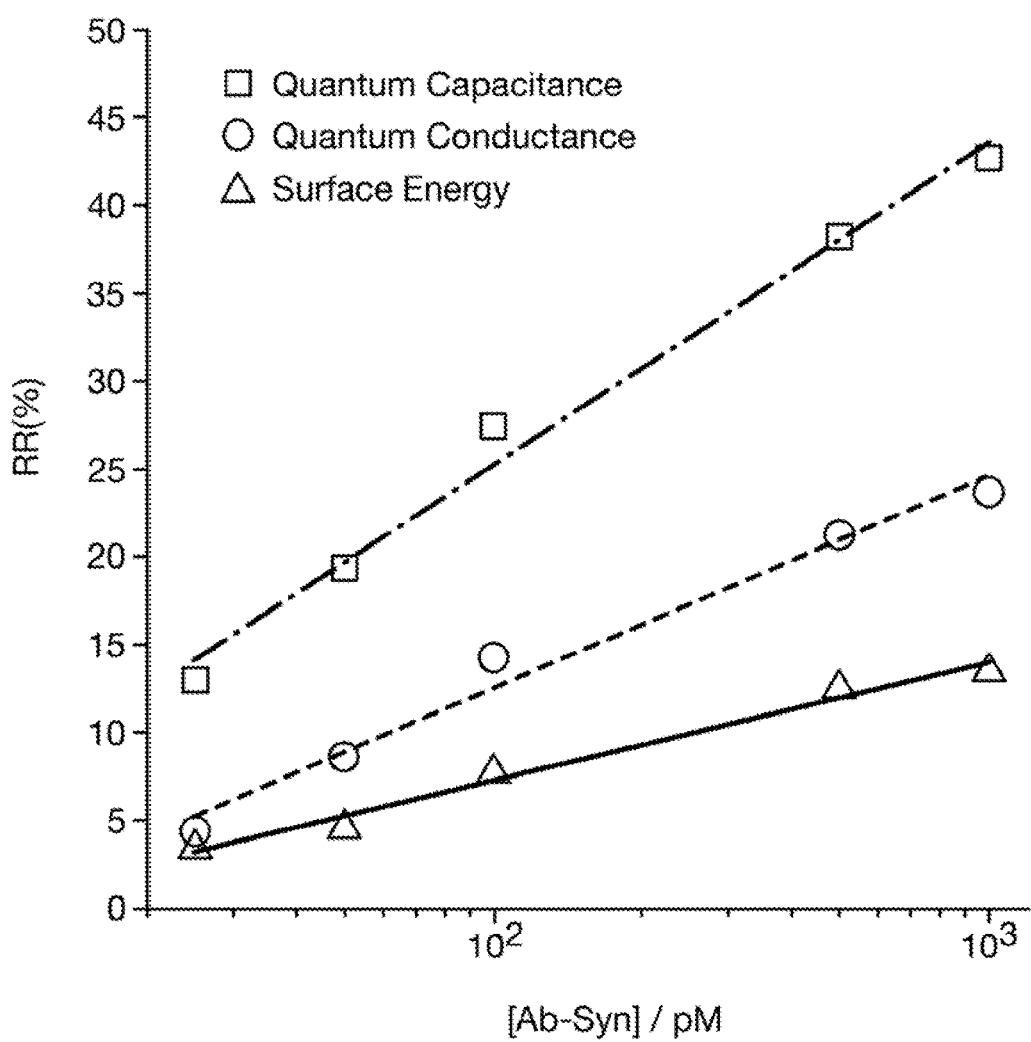
FIG. 4 is a graph of the relative response (RR) expressed as a percentage (y axis) for different concentrations of a target analyte, alpha-synuclein (α-sync), in units of pM (x axis). The graph shows comparative analytical responses on a conductive graphene layer disposed on an insulator layer on the gold substrate. The graphene layer was appropriately modified with anti-α-sync, for α-sync detection. It is evident that both quantum capacitance and quantum conductance are more sensitive than energy of the surface (as indicated in Eqn. 1 in Example 2). The sensitivity is evidenced by the slope of the assays (S). The optimal analytical frequencies for capacitance and resistance parameter are 118 and 22 Hz, respectively. Standard deviation is calculated across three measurements for each given concentration with all $r^2 \geq 0.99$.

The inventors have demonstrated that by using capacitance spectroscopy methodology it is possible to experimentally access molecular quantized states and their occupation (quantum capacitance) and to utilise this signal as a transducer for biosensor applications; this can be done because the measured capacitance is very sensitive to any change (electrostatic or chemical) of the environment. Additionally, the inventors have demonstrated that both the quantum capacitance of the system as well as the quantized resistance, communicating the quantum molecular accessible states to the electrode/probe, can be used as transducer signals. The inventors have also realised that according to Density Functional Theory (quantum mechanical methodology) The function of electron density, $E[\rho(\bar{\mu})]$, is closely related to the capacitance spectroscopy as follows $$E[\rho(\bar{\mu})] = \frac{\beta}{C_{eq}(\bar{\mu})} = \frac{\gamma}{C_q(\bar{\mu})} + \frac{\gamma'}{C_e(\bar{\mu})} \quad (1)$$

where $C_{eq}$ is the electrochemical capacitance which contains two contributions $C_q(\bar{\mu})$ (quantum) and $C_g(\bar{\mu})$ (electrostatic). It follows that any miniaturized device that contains restricted electronic states or nanoscale dimensions connected to an electrode can potentially be used in a sensory format providing that the quantum mechanical states contained in $\gamma/C_q(\bar{\mu})$ change with some external event (binding of a protein, for instance). The inventors demonstrate here, in the case of a sheet of graphene mounted over a working electrode probe, that the system can be very sensitive to such changes when a protein bound to it serves as receptor to an analyte (target protein) as illustrated in FIG. 3. In this system, the energy of the quantum mechanical states, the capacitance and the resistance (associated with the coupling between graphene electronic states and those of gold/probe electrode) can be used as transducer signals. This is illustrated in FIG. 4.

The devices were fabricated by depositing graphene oxide on the gold electrode (mechanically and electrochemically polished) through an intermediate self-assembled monolayer (insulator layer of FIG. 3, made of cysteine) by dropping a dispersion of graphene in water within an incubation time of 8 h. The receptors were attached after the CBMA, a zwitterionic monomer, was immobilized by electrostatic assembly (on the negatively charged graphene oxide terminus) on the electrode in order to create a low-fouling surface. Prior to receptive specie (anti-α-sync) immobilization, the surface modified electrodes were rinsed with $H_2O$ and dried in, a flow of nitrogen gas. The terminal carboxyl groups were then activated with 1-Ethyl-3-(3-dimethylaminopropl) carbodiimide (EDC)(0.4 M) and N-Hydroxysuccinimide (NHS) (0.1 M) ita deionized water for 40 min, and then reacted with 1 μM of the respective receptor molecule in PBS solution for 1 h, at room temperature. The interfaces were then immersed in 1 M ethanolamine (pH about 8.5) to deactivate any unreacted activated carboxylic groups and washed with PBS prior to measurements (schematically represented in FIG. 3).

The response (R) obtained for each parameter (of FIG. 4), i.e. quanrum capacitance [$C_q(\bar{\mu})$], quantum conductance [$G=kC_q(\bar{\mu})$] and surface energy (E[ρ]) [see also Eqn. (1)], were evaluated across a range of target concentration (α-sync). In order to normalize the transduction signal for each of these parameters the relative response was used. The relative response (RR), for different concentrations of target at the resonance frequency, i.e. where $k=G/C_q$ maximizes, was calculate thus as $$RR_{[target]}^R(\%) = [(R_{[target]}^k - R_0^k)/R_0^k] \times 100$$

where $R_0^k$ represents the initial value of the parameters in the absence of analyte (blank measurement) and $R_{[target]}^k$ is the value of parameter after exposing the receptor functionalized electrode to the corresponding target concentration at the same frequency k. Collecting RR over a range of target concentration, it was possible to plot the analytical curves for each the parameters as shown in FIG. 4.

The invention claimed is:

1. A sensing method for sensing a chemical substance, the method comprising:
   (A) obtaining, by electrochemical impedance spectroscopy conducted across a range of applied potentials, a plurality of measurements of the complex impedance, Z*, of a system that has a working electrode that is in contact with a carrier medium that may comprise said chemical substance, the working electrode comprising receptor moieties that are capable of binding to said chemical substance, wherein the working electrode comprises an electrode substrate functionalized with sensing elements whose electrochemical response to the applied potentials is sensitive to the binding of said chemical substance to said receptor moieties, the sensing elements having a dimension of from 0.5 to 10 nm;
   (B) converting said plurality of measurements of Z* into a plurality of measurements of the real component of the complex capacitance, C', at a selected frequency $\omega$ and/or the imaginary component of the complex capacitance, C", at a selected frequency $\omega$;
   (C) integrating the measurements of (a) C', (b) C", or (c) any combination of C' and C", at the selected frequency $\omega$ as a function of applied voltage to obtain an integrated measurement value; and
   (D) sensing whether the chemical substance is present in the carrier medium from said integrated measurement value.

2. The sensing method according to claim 1, wherein in step (A) said obtaining, by electrochemical impedance spectroscopy conducted across a range of applied potentials, a plurality of measurements of the complex impedance, comprises obtaining at least five measurements of the complex impedance at different applied potentials.

3. The sensing method according to claim 1, wherein said sensing in step (D) is performed by comparing said integrated measurement value with one or more reference values obtained by performing the steps (A), (B) and (C) under conditions where the local environment of the electrode is known.

4. The sensing method according to claim 1, wherein said chemical substance is a target species to which said receptor moieties are capable of specifically binding, and wherein said method is a method for the determining the concentration of said target species in said carrier medium.

5. The sensing method according to claim 4, wherein said target species is selected from the group consisting of CRP protein, insulin and a marker of one or more of neurodegeneration, cancer, myocardial infarction, diabetes and general trauma.

6. The sensing method according claim 1, wherein said chemical substance is selected from a lectin protein, a glycoenzyme and a carbohydrate-binding antibody, and wherein said receptor moieties are carbohydrate moieties.

7. The sensing method according to claim 6, where said working electrode forms part of a glycoarray comprising a plurality of working electrodes that are each functionalized with different carbohydrate moieties.

8. The sensing method according to claim 1, wherein said chemical substance is drug candidate and wherein said receptor moieties are moieties that are capable of binding to a reference drug.

9. The sensing method according to claim 8, wherein said working electrode forms part of an array comprising a plurality of working electrode that are each functionalized with said receptor moieties, said array thereby being suitable for use in the simultaneous screening of a plurality of drug candidates.

10. The sensing method according to claim 1, wherein said sensing elements comprise one or more of redox active species, a molecular film, nanoparticles, graphene, carbon nanotubes or quantum dots.

11. The sensing method according to claim 1, wherein said working electrode is not functionalized with a redox active species.

12. The sensing method according to claim 1, wherein said receptor moieties that are capable of binding to said chemical substance comprise an antibody or an antibody fragment.

13. The sensing method according to claim 1 wherein said sensing elements comprise graphene.

14. The sensing method according to claim 1, wherein said sensing method is a quantum capacitance sensing method.

15. An apparatus for use in a sensing method for sensing a chemical substance, which apparatus comprises:
   an electrochemical spectrometer that comprises a working electrode, a counter electrode and a potentiostat, said working electrode comprising receptor moieties that are capable of binding to said chemical substance, wherein said working electrode comprises an electrode substrate functionalized with sensing elements whose electrochemical response to applied potentials is sensitive to the binding of said chemical substance to said receptor moieties, the sensing elements having a dimension of from 0.5 to 10 nm;
   a receiver configured to receive, from said electrochemical spectrometer, input data comprising a plurality of measurements of complex impedance, Z*, across a range of applied potentials; and
   a processor configured to (i) convert said plurality of measurements of Z* into a plurality of measurements of the real component of the complex capacitance, C', at a selected frequency $\omega$ and/or the imaginary component of the complex capacitance, C", at a selected frequency $\omega$, and (ii) integrate said measurements of (a) C', (b) C", or (c) any combination of C' and C", at the selected frequency $\omega$ as a function of applied voltage to obtain an integrated measurement value.

16. The apparatus according to claim 15, further comprising an output unit configured to output data generated from said integrated measurement value.

17. A storage medium storing computer readable code for implementation by a computer or network of computers, the code, when implemented, causing the computer or network of computers to implement the steps of:
   obtaining, from an electrochemical spectrometer, input data comprising a plurality of measurements of complex impedance, Z*, across a range of applied potentials;
   converting said plurality of measurements of Z* into a plurality of measurements of the real component of the complex capacitance, C', at a selected frequency $\omega$ and/or the imaginary component of the complex capacitance, C", at a selected frequency $\omega$; and
   integrating said measurements of (a) C', (b) C", or (c) any combination of C' and C", at the selected frequency $\omega$ as a function of applied voltage to obtain an integrated measurement value.

* * * * *